United States Patent [19]

Katz

[11] 4,427,496

[45] Jan. 24, 1984

[54] METHOD FOR IMPROVING THE INSPECTION OF PRINTED CIRCUIT BOARDS

[75] Inventor: George Katz, Philadelphia, Pa.

[73] Assignee: RCA Corporation, New York, N.Y.

[21] Appl. No.: 115,379

[22] Filed: Jan. 25, 1980

[51] Int. Cl.$^3$ .............................................. G01N 27/26
[52] U.S. Cl. ................................................... 204/1 T
[58] Field of Search ............................ 204/1 T, 195 R; 339/12 R

[56] References Cited

U.S. PATENT DOCUMENTS

| | | | |
|---|---|---|---|
| 3,282,805 | 11/1966 | Brown | 204/195 R |
| 3,366,554 | 1/1968 | Lindblad | 204/1 T |
| 3,419,479 | 12/1968 | Klein | 204/1 T |
| 3,493,481 | 2/1970 | Messner et al. | 204/1 T |
| 3,494,837 | 2/1970 | Messner et al. | 204/1 T |
| 3,530,045 | 9/1970 | Alburger | 204/1 T |
| 3,810,258 | 5/1974 | Mathauser | 339/12 R |
| 4,019,129 | 4/1977 | Grau | 204/195 R |
| 4,063,644 | 12/1977 | Hoffman et al. | 204/1 T |
| 4,165,270 | 8/1979 | Ost et al. | 204/195 R |

Primary Examiner—G. L. Kaplan
Attorney, Agent, or Firm—Birgit E. Morris; Edward J. Sites

[57] ABSTRACT

An improved method is provided for the visual inspection of printed circuit boards to determine the continuity or discontinuity of the circuits. In the method the circuit boards are treated in an electrolytic bath to cause an electrochemical change in the color of the continuous circuits versus the discontinuous circuits.

7 Claims, 5 Drawing Figures

METHOD FOR IMPROVING THE INSPECTION OF PRINTED CIRCUIT BOARDS

This invention relates to a method for the inspection of printed circuit boards. More particularly, it is concerned with the method to determine the electrical continuity of printed circuits.

BACKGROUND OF THE INVENTION

In the manufacture of electronic devices, printed circuit boards are widely used both to support discrete electronic components and to provide the circuitry between the components. The printed circuit boards which are most commonly employed have a central core which is typically a dielectric material which has applied on its surface a layer of a conductive material such as a copper or silver. The conductive material may be applied to one or both of the surfaces of the core. The layer or layers of the conductive material are etched or otherwise processed to provide circuits of a predetermined geometrical configuration. Printed circuit boards are used when a large number of substantially identical devices are to be produced with a given circuit. It is important that the printed circuits be accurately reproduced from one board to another in the precise predetermined design configuration in order to obtain the required electrical performance from the fully assembled electronic devices.

In the manufacture of printed circuit boards difficulties are often encountered in accurately reproducing the required circuits on the circuit boards within the design parameters. A common problem which is encountered is that excessive amounts of the conductive material is removed or the conductive material is cracked or otherwise deformed to cause an "open" in the circuit. Another common problem which is encountered is that a portion of the conductive material which is supposed to be removed remains and a "short" develops in the circuitry. A still further problem is that often tramp conductive materials short the circuits causing defects in the electrical characteristics of the board.

One of the most commonly used methods to commercially check the quality of the circuits is to optically examine each of the circuits under relatively low magnification, for example 10X magnification, to determine if there are any deviations from the design pattern of the printed circuit. This method has proven to be relatively unsatisfactory as the quality control inspector must visually examine each of the circuits in comparison to a standard. Because of human error, numerous defective circuits are indicated to be satisfactory. A part of the problem is a result of some of the defects being relatively small and unnoticeable even under magnification. In addition, there a human fatigue factor is encountered in examining a large number of similar circuits in comparison to a standard.

The circuitry of the printed circuit boards can be electrically tested by determining the continuity or discontinuity of the circuits by providing electrical connections to each of the often hundreds of individual contact areas in a given circuit to test the continuity of the circuit. This type of electrical testing is, however, very expensive and time consuming.

It would be highly desirable if a method could be provided to improve the visual inspection of printed circuit boards to provide the accuracy and other desirable features of electrical testing.

BRIEF SUMMARY OF THE INVENTION

It has been found that the accuracy of optical inspection of the electrical circuitry on printed circuit boards to determine the electrical continuity or discontinuity of the circuitry can be substantially improved by electrochemically oxidizing or reducing the conductive metal circuitry on the printed circuit board. The electrochemical reaction is conducted in an electrolytic bath to cause a selective brightening or darkening of the continuous electrical circuitry relative to the discontinuous electrical circuitry.

DETAILED DESCRIPTION

The circuit boards which are advantageously treated for testing in accordance with the present invention are conventional in construction. Typically the circuit boards have a center core made of a dielectric material. The circuits are formed on the surfaces as noted above.

Figure 2:
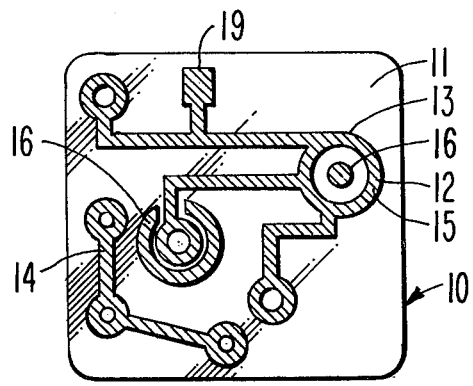
FIG. 2 is a top plan view of a typical printed circuit board prior to treatment in accordance with this invention.

In FIG. 2 there is illustrated such a typical printed circuit board 10. The printed circuit board 10 is comprised of a dielectric board 11 on which there is formed printed circuitry 12. The printed circuitry is comprised of a conductive material, usually a conductive metal such as copper or silver which, when subjected to either oxidation or reduction, will change in color. The printed circuit 14 can be formed on one side or on both sides of the dielectric board 11 and the circuitry when formed on both sides, may be interconnected by plated through holes or the like. The printed circuit board 10 which is illustrated in FIG. 2 has one repeat of the circuitry applied to the surface of the board. More typically, however, in the manufacture of printed circuits a given board will often contain many repeats of the same pattern of circuitry on a given printed circuit board 10.

For purposes of illustration, a printed circuit 12 is shown which consists of a large circuit 13 and a relatively smaller circuit 14. The larger circuit 13 has a continuous portion 15 and a discontinuous separate portion 16. Printed circuit boards such as those shown in FIG. 2 are commonly produced in the hundreds or thousands. The circuit as produced, are generally in the bright metal state such as bright copper or bright silver. It is often difficult, if not impossible, to determine with a high degree of accuracy, by optical inspection whether each of the circuits is accurately reproduced without any shorts or opens.

In accordance with the preferred embodiment of this invention, to improve the accuracy of the optical examination, the printed circuit board 10 has at least a portion of the bright metal circuitry on it subjected to oxidizing conditions to cause a selective oxidation of certain selected electrically continuous circuits on the board as will be explained in more detail below.

Figure 1:
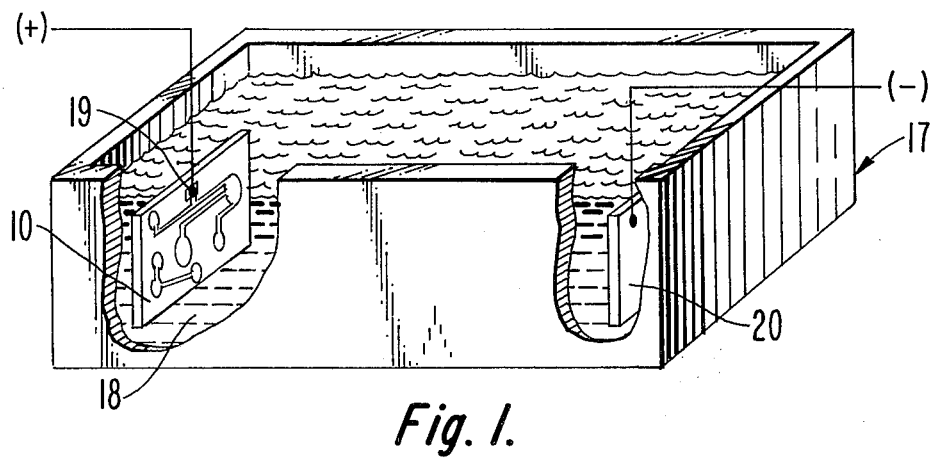
FIG. 1 is a schematic, pictorial, isometric illustration of apparatus suitable for the electrochemical treatment of printed circuit boards in accordance with this invention.

In FIG. 1 there is shown a typical type of apparatus which can be used for the purposes of this invention. The apparatus 17 is an electrolytic tank. The tank is filled with an electrolyte 18 such as a dilute, for example 5 to 25 percent by weight, water solution of an oxidizing acid like chromic acid or sulfuric acid. The printed circuit board is connected in an anodic electrode position of the tank. The connection can be made with an electrical connector such as a conventional alligator clip or the like to one or more of the large continuous circuits such as the large circuit 13 on the board 10 through a major element such as the square pad 19 of the larger circuit 13. A copper plate 20 or other similar material is connected in the cathode electrode position of the electrolytic apparatus 17.

A direct current is applied across the tank in amounts sufficient to cause a slow release of oxygen at the anode. The amount of current required is relatively low and is to some extent, dependent upon the length of time the printed circuit board is immersed in the electrolytic bath. Typically a voltage of 1 to 5 volts and an amperage of 50 to 100 milliamps with immersion of 2 to 5 minutes is more than adequate to cause sufficient oxidation to result in an easily optically observable change in color of the portions of the circuitry electrically connected to the anode from those portions which are not electrically connected with the anode.

Figure 3:
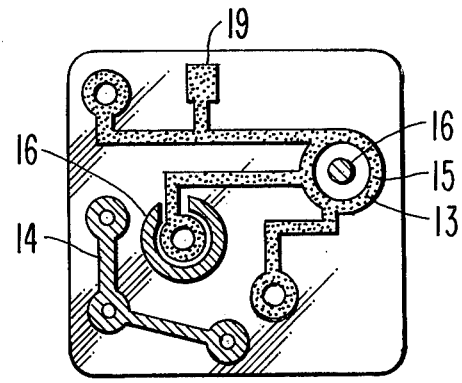
FIG. 3 is an illustration of the printed circuit board of FIG. 2 after oxidation in accordance with the teachings of this invention.

As seen in FIG. 3, a printed circuit after treatment will have the circuitry in two different colors or depths of color. As illustrated, the circuitry which was in electrical contact in the electrolytic bath was the larger continuous portion 15 of the large circuit 13. The larger portion 15, as illustrated, is oxidized to a noticeably darker color over its entire electrically continuous area showing that it was, in fact, electrically continuous as designed.

In addition, the discontinuous portions of the larger circuit 16 did not oxidize remaining in the bright metallic state being clearly distinguishable from the larger oxidized portion 15 of the larger circuit 13. This easily observable difference simplifies the optical examination to determine whether the continuous portion 15 of the circuit is, in fact, electrically continuous as it was designed and if the discontinuous portion 16 is electrically separated from the larger portion 15 of the circuit.

It can be seen from a comparison of FIGS. 2 and 3 that the visual examination for electrical continuity or discontinuity has been simplified and made more accurate by employment of the method of this invention.

Figure 4:
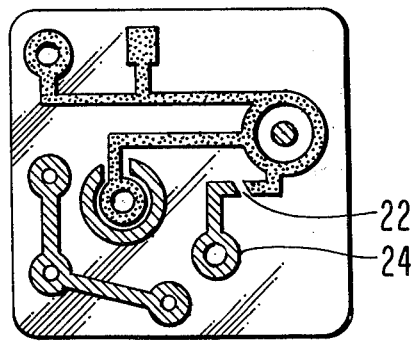
FIG. 4 is an illustration similar to the printed circuit board of FIG. 2 which has been modified to provide an open in the circuitry and thereafter subjected to oxidation.

For purposes of further illustration in FIG. 4, a break 22 was put into the larger circuit 13. It can be seen that the lead and pad 24 did not oxidize to the darker color. As a result of employing the method of this invention this defect is more easily detectable by visual comparison with the standard.

Figure 5:
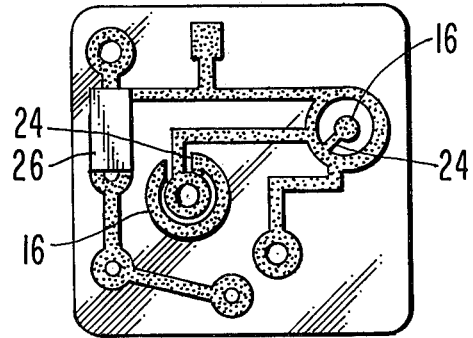
FIG. 5 is an illustration similar to the printed circuit board of FIG. 2 which has been modified to include shorts in the printed circuitry and by causing shorts by external means and then subjected to oxidation.

In FIG. 5 shorts 24 were left in the circuitry. As a result of leaving the shorts 24 in the circuitry, the heretofore discontinuous portions 16 were oxidized and darkened in the electrolytic bath. This test clearly shows the undesirable continuity from the designed continuous and discontinuous pattern. In use the operator can often, by use of suitable tools, remove the shorts and thereby salvage the circuit board.

In most situations it is desirable to have both oxidized continuous circuits and unoxidized discontinuous areas of circuitry to assist in the evaluation of the circuitry. However, in certain situations, it is desirable to connect together for test purposes all the various areas of the circuitry on the board which in actual application will be discontinuous. This can be done by making temporary connections by soldering leads between the areas of the circuitry on the board or by using other methods such as conductive paste and the like. The use of these methods have, however, proven to be both time consuming and expensive and have been found to cause further problems in continuing the processing of the boards at a later stage if the temporary connections are not completely removed. It has been found, and it is one of the further features of this invention, that when it is desired to make temporary connections between otherwise isolated portions of circuitry on a given board or repeats of circuits on a given printed circuit board for test purposes, that the preferred method is to use a pair of magnets with one magnet 26 being on the face side in connection with the separated circuitry and another magnet (not shown) on the opposite side to hold it in place. The magnets are sufficient to provide sufficient conductivity of the current for test purposes and after the test is completed can be readily removed without damage to the circuitry on the boards.

After the circuit boards 10 have been oxidized as noted above and the electrical continuity or discontinuity as desired is checked by optical or mechanical means to identify defective parts, the printed circuit board is generally subjected to a conventional cleaning bath to remove the relatively thin oxide coating and provide bright metal conductors for further processing such as soldering of electronic components to the circuitry.

The above-described method to improve the optical inspection of printed circuit boards is clearly the preferred method. It should be appreciated, however, that variations can be made in the method without departing from the scope of this invention. For example, an alternate method of conducting the electrochemical treatment is to initially oxidize the entire conductive metal circuitry and then connect the continuous circuit in the cathodic position. In this mode the continuous area of circuitry are chemically reduced to a bright state.

What is claimed is:

1. A method for improving the optical examination of printed circuit boards to determine the electrical continuity of at least a portion of the circuitry on the printed circuit board comprising the steps of electrically connecting at least a portion of the circuitry of said printed circuit board in a first electrode position of a first polarity, immersing said printed circuit board into an electrolytic bath, immersing a second electrode of the opposite polarity in said bath, passing a direct electric current between said first electrode and said second electrode through said electrolytic bath in an amount sufficient to cause a change in the state of oxidation of the exposed surface of the circuitry connected in the first electrode position whereby the portion of the circuitry in continuous electrical connection in the first electrode position is electrochemically changed in color so as to be more easily optically distinguished from a portion of the circuit not in electrical continuity.

2. The processing according to claim 1, wherein said circuitry is comprised of conductive metal in a bright state, said circuitry being connected in the anodic position and wherein said direct current is conducted through said bath until a portion of the circuitry in electrical contact as the anode is oxidized to a darker, optically distinguishable form from circuitry in said bright state.

3. The process according to claim 2, wherein said circuitry is comprised of metallic copper.

4. The process according to claim 3, wherein the current is from about 1 to 5 volts and from about 50 to 100 millamperes.

5. The process according to claim 1, wherein said circuitry has a plurality of electrically discontinuous portions and wherein said portions are temporarily connected together with the electrically continuous portion during the electrochemical reaction.

6. The process according to claim 5, wherein the connecting means employed is magnets.

7. The process according to claim 1, wherein the entire circuitry is initially oxidized to a first darker color and thereafter a portion of said circuitry is electrically connected as the cathodic electrode in the electrolytic bath and said current is conducted through said bath until the electrically connected portions of the printed circuitry is electrochemically reduced to an optically distinguishable bright metal state.

* * * * *